(12) United States Patent
Wada et al.

(10) Patent No.: US 10,118,940 B2
(45) Date of Patent: Nov. 6, 2018

(54) ALKOXIDE COMPOUND AND RAW MATERIAL FOR FORMING THIN FILM

(75) Inventors: Senji Wada, Tokyo (JP); Akio Saito, Tokyo (JP); Tomoharu Yoshino, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 14/115,495

(22) PCT Filed: May 15, 2012

(86) PCT No.: PCT/JP2012/062390
§ 371 (c)(1),
(2), (4) Date: Nov. 4, 2013

(87) PCT Pub. No.: WO2013/018413
PCT Pub. Date: Feb. 7, 2013

(65) Prior Publication Data
US 2014/0174323 A1 Jun. 26, 2014

(30) Foreign Application Priority Data
Aug. 2, 2011 (JP) ................................ 2011-169103

(51) Int. Cl.
| | |
|---|---|
| C07F 15/04 | (2006.01) |
| C23C 16/06 | (2006.01) |
| C23C 16/40 | (2006.01) |
| C23C 16/455 | (2006.01) |
| C07C 215/08 | (2006.01) |

(52) U.S. Cl.
CPC .......... *C07F 15/045* (2013.01); *C07C 215/08* (2013.01); *C23C 16/06* (2013.01); *C23C 16/406* (2013.01); *C23C 16/45553* (2013.01)

(58) Field of Classification Search
None
See application file for complete search history.

(56) References Cited

U.S. PATENT DOCUMENTS

| | | | |
|---|---|---|---|
| 7,462,732 B2 | 12/2008 | Kim et al. | |
| 7,501,153 B2 | 3/2009 | Yamada et al. | |
| 2007/0122947 A1 | 5/2007 | Sakurai et al. | |
| 2008/0085365 A1* | 4/2008 | Yamada et al. | 427/255.28 |
| 2008/0171890 A1 | 7/2008 | Kim et al. | |

FOREIGN PATENT DOCUMENTS

| | | |
|---|---|---|
| JP | 2006-143693 | 6/2006 |
| JP | 2008-537947 | 10/2008 |
| WO | WO 2005/063685 | 7/2005 |
| WO | 2006021850 | 3/2006 |
| WO | 2006107121 | 10/2006 |

OTHER PUBLICATIONS

Taek Seung Yang et al., Atomic layer deposition of nickel oxide films using Ni(dmamp)2 and water; J. Vac. Sci. Technol. A, vol. 23, No. 4, Jul./Aug. 2005 1238-1243.
International Search Report, PCT/JP2012/062390, Jul. 3, 2012.
Werndrup, Pia et al., A single-source-precursor approach to late transition metal molybdate materials: the structural role of chelating ligands in the formation of heterometallic heteroleptic akloxide complexes, European Journal of Inorganic Chemistry, 2006, (7), p. 1413-1422.

* cited by examiner

*Primary Examiner* — Yun Qian
(74) *Attorney, Agent, or Firm* — Young & Thopson

(57) ABSTRACT

An alkoxide compound represented by the following formula (I), and a raw material for thin film formation containing the alkoxide compound. In the formula, $R^1$ represents a linear or branched alkyl group having 2 to 4 carbon atoms, and $R^2$ and $R^3$ each represent a linear or branched alkyl group having 1 to 4 carbon atoms. In the formula (I), $R^1$ is preferably an ethyl group. It is also preferred that one or both of $R^2$ and $R^3$ be an ethyl group. The raw material for thin film formation including an alkoxide compound represented by general formula (I) is preferably used as a raw material for chemical vapor deposition.

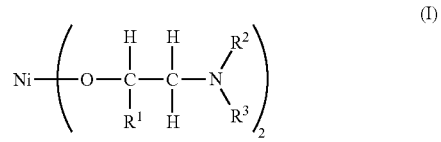

13 Claims, 2 Drawing Sheets

ALKOXIDE COMPOUND AND RAW MATERIAL FOR FORMING THIN FILM

TECHNICAL FIELD

The present invention relates to a novel nickel alkoxide compound having a specific ligand, and a raw material for thin film formation comprising the compound.

BACKGROUND ART

A thin film containing nickel is mainly used for a member of an electronic component, such as a resistance film and a barrier film, a member for recording media, such as a magnetic film, a member for a thin film solar cell, such as an electrode, etc.

Processes for forming the above-described thin film include flame hydrolysis deposition, sputtering, ion plating, MOD techniques including dipping-pyrolysis process and sol-gel process, and chemical vapor deposition. Chemical vapor deposition (hereinafter sometimes abbreviated as CVD) processes inclusive of ALD (atomic layer deposition) are the most suitable for many advantages, such as compositional controllability, excellent step coverage, suitability to large volume production, and capability of hybrid integration.

MOD and CVD processes use a compound having an organic ligand as a precursor supplying nickel atoms to a thin film. Patent Literature 1 reports a tertiary alkoxide compound of nickel, and Patent Literature 2 reports a method for producing a mixed oxide thin film containing nickel atoms and prepared by a CVD process using an alkoxide of nickel. In addition, Non-Patent Literature 1 reports the preparation of a nickel oxide film by an ALD process using a tertiary alkoxide compound of nickel.

As to nickel compounds, no reports are made to the secondary alkoxide compound of the present invention and no reports are also made to a method for producing a thin film using the same.

CITATION LIST

Patent Literature

Patent Literature 1: WO 2006/107121 A1
Patent Literature 2: WO 2006/021850 A2

NON-PATENT LITERATURE

Non-Patent Literature 1: J. Vac. Sci. Technol. A, Vol. 23, No. 4, July/August 2005 1238-1243

SUMMARY OF INVENTION

Technical Problem

In the method for forming a thin film by vaporizing a compound (precursor) such as a CVD process, properties which the compound is required to have include being low in melting point and able to be transferred in a liquid state, and being high in vapor pressure and easy to vaporize. Conventional nickel compounds are ones which are not fully satisfactory in these aspects.

Solution to Problem

As a result of extensive investigations, the present inventors have found that an alkoxide compound having a specific secondary amino alcohol as a ligand can solve the above problem and thus reached the present invention.

The present invention provides an alkoxide compound represented by the following formula (I).

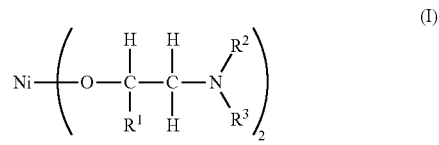

(in the formula, $R^1$ represents a linear or branched alkyl group having 2 to 4 carbon atoms, and $R^2$ and $R^3$ each represent a linear or branched alkyl group having 1 to 4 carbon atoms.)

In addition, the present invention provides a raw material for thin film formation comprising an alkoxide compound represented by the above formula (I).

Effect of Invention

The present invention can afford a low-melting nickel alkoxide compound that has a high vapor pressure and that turns into a liquid at normal temperature or upon slight heating. The use of the compound as a source material for thin film formation by a CVD process can provide good ability to transfer a precursor in the course of producing a nickel-containing thin film by a CVD process, can provide easy control of the supplied amount to a base material, and can stably supply a source material for thin film formation to the base material.

DESCRIPTION OF EMBODIMENTS

Figure 1:
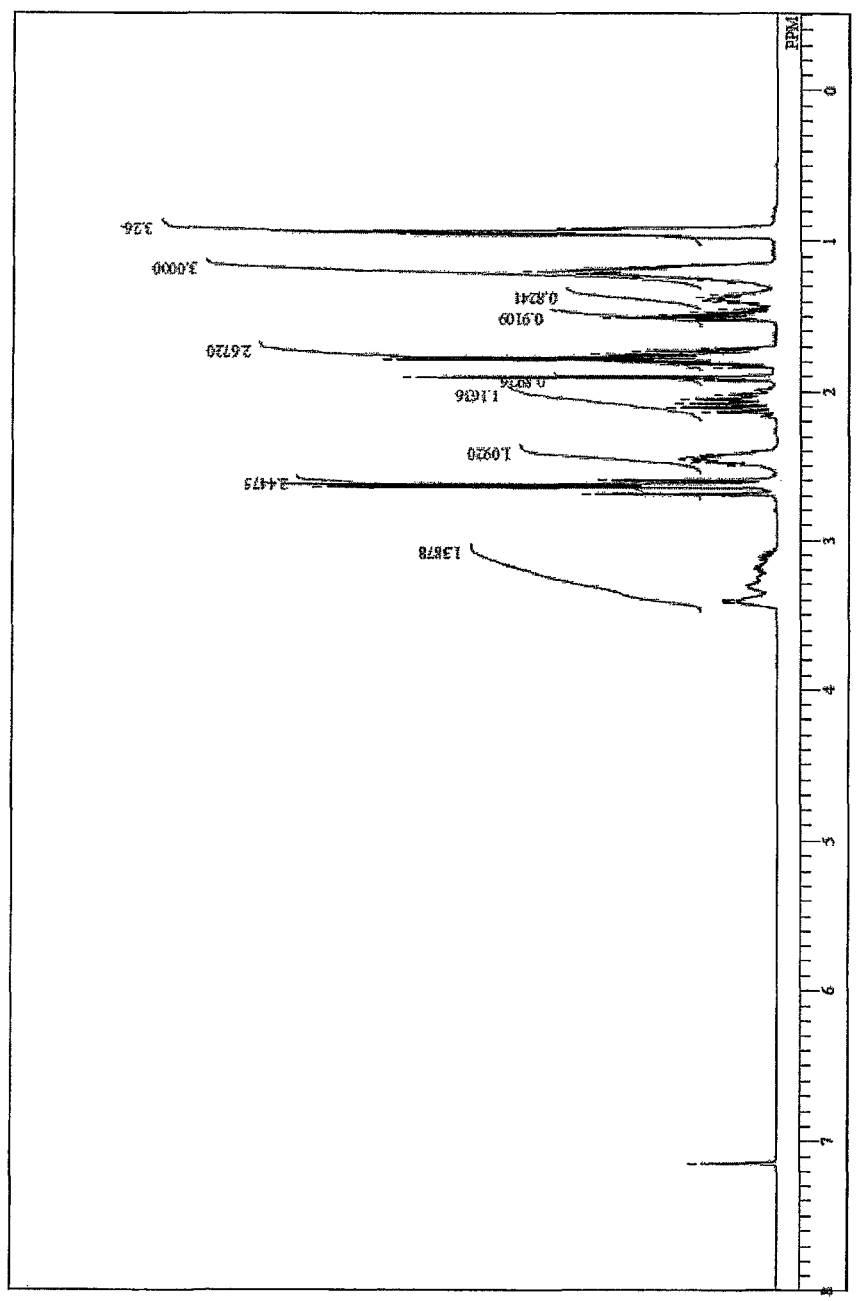
FIG. 1 is an NMR chart of the Compound No. 4 obtained in Example 3.

Hereinafter, the alkoxide compound of the present invention and a raw material for thin film formation comprising the compound will be explained in detail based on preferable exemplary embodiments.

Examples of the linear or branched alkyl group having 2 to 4 carbon atoms represented by $R^1$ in the above formula (I) include ethyl, propyl, isopropyl, butyl, sec-butyl, tert-butyl, and isobutyl, and examples of the linear or branched alkyl group having 1 to 4 carbon atoms represented by $R^2$ and $R^3$ include methyl, ethyl, propyl, isopropyl, butyl, sec-butyl, tert-butyl, and isobutyl. Some alkoxide compounds of the present invention have optical isomers, which, however, are not distinguished by their isomeric configuration.

Regarding $R^1$ to $R^3$ in the above formula (I), when used for a method for forming a thin film including a step of vaporizing a compound, the compound is preferably one that is in a liquid state under normal temperature and normal pressure and has a high vapor pressure. Specifically, $R^1$ is preferably an ethyl group and one or both of $R^2$ and $R^3$ is preferably an ethyl group. On the other hand, when used for a method for forming a thin film by MOD involving no vaporization step, $R^1$ to $R^3$ may be selected appropriately according to the solubility in the solvent to be used, the thin film formation reaction, etc.

The case where the terminal donor group of the ligand is coordinated to a metal atom to form a cyclic structure is shown in the following formula (II). The alkoxide compound of the present invention, which is shown herein representatively by the above formula (I) but is not distinguished from the following formula (II), includes compound represented by any of the formula (I) and (II).

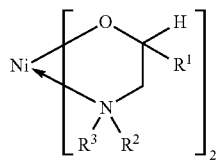
(II)

(In the formula, $R^1$ represents a linear or branched alkyl group having 2 to 4 carbon atoms, and $R^2$ and $R^3$ each represent a linear or branched alkyl group having 1 to 4 carbon atoms.)

Specific examples of the alkoxide compound of the present invention include the following Compounds No. 1 to No. 18. It is noted that the present invention is not limited at all by the following exemplary compounds.

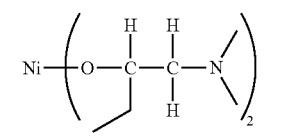
Compound No. 1

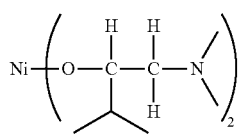
Compound No. 2

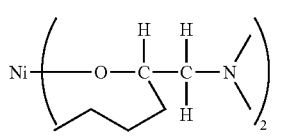
Compound No. 3

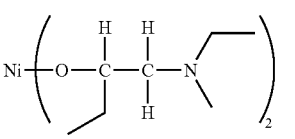
Compound No. 4

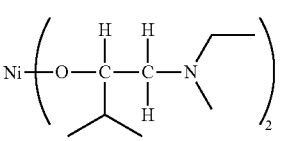
Compound No. 5

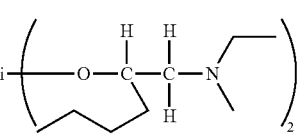
Compound No. 6

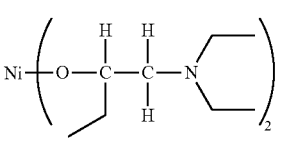
Compound No. 7

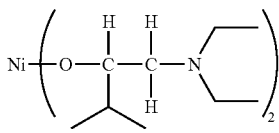
Compound No. 8

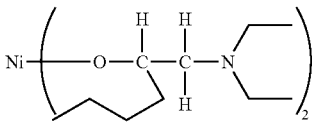
Compound No. 9

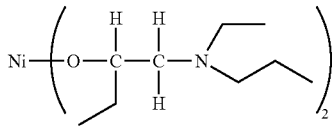
Compound No. 10

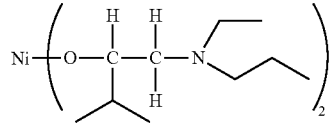
Compound No. 11

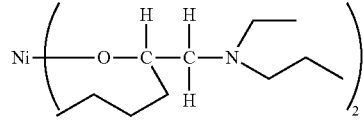
Compound No. 12

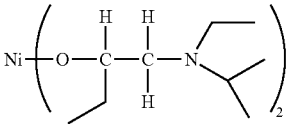
Compound No. 13

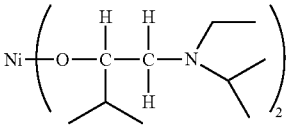
Compound No. 14

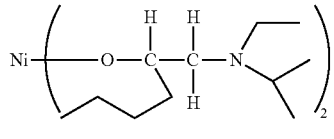
Compound No. 15

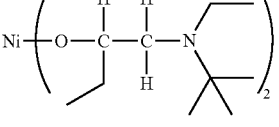
Compound No. 16

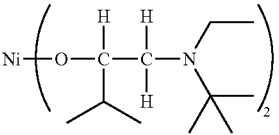
Compound No. 17

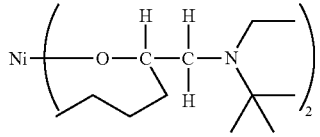
Compound No. 18

The alkoxide compound of the present invention is not limited by the process of the preparation thereof and can be prepared by using well-known reactions. Well-known common synthetic methods of alkoxide compounds using the corresponding aminoalcohols can be applied. Such synthetic methods include, for example, a method in which an inorganic salt such as halides and nitrate of nickel or hydrate thereof is reacted with the corresponding alcohol in the presence of a base such as sodium, sodium hydride, sodium amide, sodium hydroxide, sodium methylate, ammonia, and amines, a method in which an inorganic salt such as halides and nitrate of nickel or hydrate thereof is reacted with an alkali metal alkoxide such as sodium alkoxide, lithium alkoxide, and potassium alkoxide derived from the corresponding alcohol compound, a method in which an alkoxide compound derived from a low-molecular-weight alcohol such as nickel methoxide, ethoxide, isopropoxide, and butoxide is subjected to exchange reaction with the corresponding alcohol compound, and a method in which an inorganic salt such as halides and nitrate of nickel is reacted with a derivative that gives a reactive intermediate to obtain the reactive intermediate, followed by reacting this with the corresponding alcohol compound.

Examples of the reactive intermediate include nickel amide compounds such as bis(dialkylamino)nickel and bis(bis(trimethylsilyl)amino)nickel.

The alkoxide compound of the present invention is characterized by being a secondary alkoxide compound, and the alkoxide compound of the present invention exhibits specific properties whereas tertiary alkoxide compounds have superior characteristics in Cu, Ti, Zr, Hf complexes having an aminoalkoxide as a ligand.

The alkoxide compound of the present invention can be used as a precursor for producing a thin film containing nickel and also can be used for such applications as catalysts for organic synthesis, source materials for organic synthesis, etc.

The raw material for thin film formation of the present invention contains the alkoxide compound of the present invention described above as a precursor of a thin film. The form of the raw material may vary depending upon the production process to which the raw material for thin film formation will be applied. The alkoxide compound of the present invention is particularly useful as a raw material for chemical vapor deposition because of its physical properties. That is, the raw material for thin film formation of the present invention is preferably a raw material for chemical vapor deposition.

When the raw material for thin film formation of the present invention is a raw material for chemical vapor deposition, the form thereof is chosen appropriately depending upon the techniques for a material delivering and feeding method and others in the chemical vapor deposition process to be used. Representative examples of the raw material for thin film formation of the present invention when it is used as a raw material for chemical vapor deposition include the following (1) and (2).

(1) A raw material for thin film formation comprising a precursor itself comprising the alkoxide compound of the present invention, wherein the precursor excluding the alkoxide compound is in a proportion of from 0 to 10 mol per mol of the alkoxide compound, and the raw material is delivered and fed by a vapor delivery method or a liquid delivery method in thin film production.

(2) A raw material for thin film formation comprising an organic solvent and a precursor comprising the alkoxide compound of the present invention, wherein the content of the precursor comprising the alkoxide compound is 0.01 to 2.0 mol/liter, the precursor excluding the alkoxide compound is in a proportion of from 0 to 10 mol per mol of the alkoxide compound, and the raw material is delivered and fed by a liquid delivery method in thin film production.

A more detailed description is made to the raw material for thin film formation of the present invention in the case of being used as a raw material for chemical vapor deposition.

The delivering and feeding method includes a vapor delivery method in which a raw material for chemical vapor deposition is vaporized by heating and/or reducing pressure in a source reservoir and the resulting vapor is introduced into the deposition reaction chamber optionally together with a carrier gas such as argon, nitrogen, and helium; and a liquid delivery method in which a raw material for chemical vapor deposition is delivered in a liquid or solution state to a vaporization chamber, vaporized by heating and/or reducing pressure in the vaporization chamber, and introduced into the deposition reaction chamber. In the vapor delivery method, the raw material for chemical vapor deposition is the alkoxide compound represented by general formula (I) itself, while in the liquid delivery method, the raw material for chemical vapor deposition is the alkoxide compound represented by general formula (I) itself or a solution containing the alkoxide compound dissolved in an organic solvent.

Chemical vapor deposition processes for multi-component systems include a technique in which each component composing a raw material for chemical vapor deposition is separately vaporized and fed (hereinafter may be also called "single source method") and a technique in which a mixed source obtained by pre-mixing a plurality of source components at a desired ratio is vaporized and fed (hereinafter may be also called "cocktail source method"). In the cocktail source method, the raw material for chemical vapor deposition is a mixture or mixed solution containing two or more alkoxide compounds of the present invention, or a mixture or mixed solution containing one or more alkoxide compounds of the present invention and one or more other precursor(s). In the event that a mixture or a mixed solution of an alkoxide compound of the present invention with other precursor(s) is used as a raw material for chemical vapor deposition, while their mixing ratio is appropriately chosen depending upon the desired thin film composition, it is commonly preferred to choose the amount of the other precursor(s) from the range of 0.01 to 10 mol, and more preferably from the range of 0.1 to 5 mol, per 1 mol of the alkoxide compound of the present invention.

There is no particular limitation on the organic solvent used in the aforementioned material for CVD, and any organic solvent generally known may be used. Such organic solvents include acetates such as ethyl acetate, butyl acetate, and methoxyethyl acetate; ether alcohols such as ethylene glycol monomethyl ether, ethylene glycol monoethyl ether, ethylene glycol monobutyl ether, and diethyleneglycol monomethyl ether; ethers such as tetrahydrofuran, tetrahydropyran, ethylene glycol dimethyl ether, diethylene glycol dimethyl ether, triethylene glycol dimethyl ether, dibutyl ether, and dioxane; ketones such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons such as hexane, cyclohexane, methylcyclohexane, dimethylcyclohexane, ethylcyclohexane, heptane, octane, toluene, and xylene; cyanohydrocarbons such as 1-cyanopropane, 1-cyanobutane, 1-cyanohexane, cyanocyclohexane, cycanobenzene, 1,3-dicyanopropane, 1,4-dicyanobutane, 1,6-dicyanohexane, 1,4-dicyanocyclohexane, and 1,4-dicyanobenzene; pyridine and lutidine. These are used alone or as a mixed solvent of two or more of them, depending on solubility of the solute, and relationships between the temperature in use and the boiling point and flash point of the solvent. When such an organic solvent is used, the total amount of the alkoxide compound of the present invention and the other precursor(s) in the organic solvent is preferably adjusted to 0.01 to 2.0 mol/liter, particularly 0.05 to 1.0 mol/liter.

In CVD processes for multi-component systems, any well-known common precursor used as a CVD source may be used as the other precursor(s) to be used together with the alkoxide compound of the present invention without particular limitations.

Examples of the other precursor(s) include compounds of silicon or metal with one or two or more organic coordination compounds selected from alcohol compounds, glycol compounds, β-diketone compounds, cyclopentadiene compounds, and organic amine compounds. Examples of the metal in a precursor includes magnesium, calcium, strontium, barium, titanium, zirconium, hafnium, vanadium, niobium, tantalum, chromium, molybdenum, tungsten, manganese, iron, ruthenium, cobalt, rhodium, iridium, nickel, palladium, platinum, copper, silver, gold, zinc, aluminum, gallium, indium, germanium, tin, lead, antimony, bismuth, yttrium, lanthanum, cerium, praseodymium, neodymium, promethium, samarium, europium, gadolinium, terbium, dysprosium, holmium, erbium, thulium, and ytterbium.

Alcohol compounds used as the organic coordination compound include alkyl alcohols such as methanol, ethanol, propanol, isopropanol, butanol, 2-butanol, isobutanol, tert-butanol, amyl alcohol, isoamyl alcohol, and tert-amyl alcohol; ether alcohols such as 2-methoxyethanol, 2-ethoxyethanol, 2-butoxyethanol, 2-(2-methoxyethoxy)ethanol, 2-methoxy-1-methylethanol, 2-methoxy-1,1-dimethylethanol, 2-ethoxy-1,1-dimethylethanol, 2-isopropoxy-1,1-dimethylethanol, 2-butoxy-1,1-dimethylethanol, 2-(2-methoxyethoxy)-1,1-dimethylethanol, 2-propoxy-1,1-diethylethanol, 2-sec-butoxy-1,1-diethylethanol, and 3-methoxy-1,1-dimethylpropanol; and dialkylaminoalcohols which provide the alkoxide compound of the present invention.

Glycol compounds used as the organic coordination compound include 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, 2,4-hexanediol, and 2,4-dimethyl-2,4-pentanediol.

Examples of the β-diketone compounds to be used as the organic coordination compound include alkyl-substituted β-diketones such as acetylacetone, hexane-2,4-dione, 5-methylhexane-2,4-dione, heptane-2,4-dione, 2-methylheptane-3,5-dione, 5-methylheptane-2,4-dione, 6-methylheptane-2,4-dione, 2,2-dimethylheptane-3,5-dione, 2,6-dimethylheptane-3,5-dione, 2,2,6-trimethylheptane-3,5-dione, 2,2,6,6-tetramethylheptane-3,5-dione, octane-2,4-dione, 2,2,6-trimethyloctane-3,5-dione, 2,6-dimethyloctane-3,5-dione, 2,9-dimethylnonane-4,6-dione, 2-methyl-6-ethyldecane-3,5-dione, and 2,2-dimethyl-6-ethyldecane-3,5-dione; fluorinated alkyl β-diketones such as 1,1,1-trifluoropentane-2,4-dione, 1,1,1-trifluoro-5,5-dimethylhexane-2,4-dione, 1,1,1,5,5,5-hexafluoropentane-2,4-dione, and 1,3-diperfluorohexylpropane-1,3-dione; ether-substituted β-diketones such as 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione.

Examples of the cyclopentadiene compounds to be used as the organic coordination compound include cyclopentadiene, methylcyclopentadiene, ethylcyclopentadiene, propylcyclopentadiene, isopropylcyclopentadiene, butylcyclopentadiene, sec-butylcyclopentadiene, isobutylcyclopentadiene, tert-butylcyclopentadiene, dimethylcyclopentadiene, and tetramethylcyclopentadiene.

Examples of the organic amine compounds to be used as the organic coordination compound include methylamine, ethylamine, propylamine, isopropylamine, butylamine, sec-butylamine, tert-butylamine, isobutylamine, dimethylamine, diethylamine, dipropylamine, diisopropylamine, ethylmethylamine, propylmethylamine, and isopropylmethylamine.

In the case of the single source method, the aforementioned other precursor(s) is preferably a compound that exhibits a thermal and/or oxidative decomposition behavior similar to that of the alkoxide compound of the present invention, and in the case of the cocktail source method, preferred is a compound that not only exhibits a similar thermal and/or oxidative decomposition behavior but also fails to cause degradation due to chemical reactions during mixing.

It is allowed to make the raw material for thin film formation of the present invention optionally contain a nucleophilic reagent in order to impart the stability of the alkoxide compound of the present invention and other precursor(s). The nucleophilic reagent includes ethylene glycol ethers such as glyme, diglyme, triglyme and tetraglyme; crown ethers such as 18-crown-6, dicyclohexyl-18-crown-6, 24-crown-8, dicyclohexyl-24-crown-8, and dibenzo-24-crown-8; polyamines such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine and triethoxytriethyleneamine; cyclic polyamines such as cyclam and cyclen; heterocyclic compounds such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole and oxathiolane; β-ketoesters such as acetoacetic acid methyl ester, acetoacetic acid ethyl ester, and acetoacetic acid-2-methoxyethyl ester; and β-diketones such as acetylacetone, 2,4-hexanedione, 2,4-heptanedione, 3,5-heptanedione and dipivaloylmethane. The use amount of these nucleophilic reagents as stabilizers is preferably within the range of from 0.1 mol to 10 mol, and more preferably from 1 to 4 mol, per mol of the precursor.

In the raw material for thin film formation of the present invention, there should be minimized contamination with substances other than components thereof including metal element impurities, halogen impurities such as chlorine-containing impurities, and organic impurities. The content of the metal element impurities is preferably 100 ppb or less, and more preferably 10 ppb or less for each element and is preferably 1 ppm or less, and more preferably 100 ppb or less in total. Especially, when using the raw material to make a gate dielectric layer, a gate layer, or a barrier layer of LSI, it is necessary to reduce the content of alkali metal elements, alkaline earth metal elements, and same group elements which affect the electric properties of a thin film to be obtained. The amount of the halogen impurities is preferably 100 ppm or less, more preferably 10 ppm or less, and even more preferably 1 ppm or less. The total content of organic impurities is preferably not more than 500 ppm, more preferably not more than 50 ppm, and even more preferably not more than 10 ppm. Since water causes particle generation in a raw material for chemical vapor deposition or particle generation during thin film formation, it is recommended for each of the metal compound, the organic solvent, and the nucleophilic reagent to remove water as much as possible prior to use in order to reduce the water content thereof In each of the metal compound, the organic solvent, and the nucleophilic reagent, the water content is preferably not more than 10 ppm and more preferably not more than 1 ppm.

In the raw material for thin film formation of the present invention, it is preferred to minimize contamination with particles as much as possible in order to reduce or prevent the particle pollution of a thin film to be formed. Specifically, in particle measurement with a light-scattering submerged particle detector in a liquid phase, the number of particles larger than 0.3 μm is preferably 100 or less in 1 ml of the liquid phase, more preferably the number of particles larger than 0.2 μm is 1000 or less in 1 ml of the liquid phase, and even more preferably the number of particles larger than 0.2 μm is 100 or less in 1 ml of the liquid phase.

The method of using the raw material for thin film formation of the present invention in the case where the material is used as a raw material for chemical vapor deposition (i.e., a thin film production method) is described concretely below. This thin film production method is a method using a chemical vapor deposition process in which a vapor produced by vaporizing the alkoxide compound of the present invention and other precursor(s) optionally used is introduced optionally with a reactive gas optionally used onto a substrate, and these precursors are then decomposed and/or reacted on the substrate, so that a thin film is grown and deposited on the substrate. A catalyst can be used during the chemical vapor deposition process, and the method of delivering and feeding raw materials, the deposition method, production conditions, production apparatuses, etc. are not particularly restricted, and there may be employed common conditions and methods.

Examples of the reactive gas optionally used include oxidative ones, such as oxygen, ozone, nitrogen dioxide, nitrogen monoxide, water vapor, hydrogen peroxide, formic acid, acetic acid, and acetic anhydride; reductive ones, such as hydrogen, ammonia, and organometallic compounds; and nitriding agents including organic amine compounds such as monoalkylamines, dialkylamines, trialkylamines, and alkylenediamines, hydrazine, and ammonia.

Examples of the above-mentioned catalyst include high-melting metals, such as tungsten.

Examples of the aforementioned delivering and feeding methods includes the aforementioned vapor delivery methods, liquid delivery methods, cocktail source methods, single source methods, and others.

The aforementioned deposition methods include the thermal CVD process in which material gas or material gas and reactive gas are reacted only by heat in order to deposit a thin film; the plasma CVD process in which heat and plasma are used; the photo-excited CVD process in which heat and light are used; the photo and plasma-excited CVD process in which heat, light and plasma are used; and the ALD process in which the CVD deposition reaction is separated into elementary steps and deposition is carried out step by step in a molecular level.

The formation conditions include the reaction temperature (substrate temperature), reaction pressure, deposition rate, and the like. The reaction temperature is preferably 100° C. or higher, at which the alkoxide compound of the present invention is sufficiently reactive, and more preferably 150° C. to 300° C. The reaction pressure is preferably from atmospheric pressure to 10 Pa for the thermal CVD and photo-excited CVD processes, and when plasma is used, it is preferably from 2,000 Pa to 10 Pa.

The deposition rate may be controlled by the supply conditions (vaporization temperature and vaporization pressure) of the material and the reaction temperature and pressure. Since excessively high deposition rates may result in deteriorating the properties of the resulting thin film and too low deposition rates may cause a problem in productivity, the deposition rate is preferably 0.01 to 5000 nm/min and more preferably 0.1 to 1000 nm/min. In ALD, the number of cycles is controlled so as to obtain a desired film thickness.

For example, in the case of forming a nickel film by a CVD process, a vapor formed by vaporizing the alkoxide compound of the present invention and other precursor(s) to be optionally used, and a reactive gas to be optionally used are first introduced onto a substrate in a deposition reaction chamber as described above (raw material introduction step). Preferably, the alkoxide compound of the present invention is vaporized at room temperature to 200° C. The pressure at which the alkoxide compound of the present invention is vaporized is preferably 0.01 to 300 Pa. Following the above-described raw material introduction step, a precursor thin film is formed on the substrate from the nickel alkoxide compound introduced into the deposition reaction chamber (precursor thin film formation step). At this time, heat may be added by heating the substrate or heating the deposition reaction chamber. The precursor thin film formed in this step is a nickel thin film or a thin film formed through decomposition and/or reaction of part of the nickel alkoxide compound and has a different composition from the target nickel thin film. The temperature at which this step is conducted is preferably room temperature to 400° C., and more preferably 150 to 300° C.

Subsequently, unreacted nickel alkoxide compound gas and by-produced gas are exhausted from the deposition reaction chamber (exhaustion step). Although the unreacted nickel alkoxide compound gas and the by-produced gas are ideally exhausted completely from the deposition reaction chamber, complete exhaustion is not always required. Examples of the method of exhaustion include a method in which the system is purged with an inert gas such as helium and argon, a method in which exhaustion is achieved by reducing the pressure in the system, and a method in which these are combined. The magnitude of reduced pressure in reducing the pressure is preferably 0.01 to 300 Pa, and more preferably 0.01 to 100 Pa.

Subsequently, a reducing gas is introduced into the deposition reaction chamber, and then by the action of the reducing gas or the reducing gas and heat, a nickel thin film is formed from the precursor thin film formed in the preceding precursor thin film formation step (nickel thin film formation step). The temperature at which heat is applied in this step is preferably room temperature to 400° C., and more preferably 150 to 300° C. The alkoxide compound of the present invention has good reactivity with reducing gas and can afford a nickel thin film.

A cycle of thin film deposition is composed of a series of operations consisting of the above-described raw material introduction step, precursor thin film formation step, exhaustion step, and nickel thin film formation step. The cycle may be repeated a plurality of times until a thin film having a necessary thickness is obtained (ALD process). In this case, preferably, after the execution of one cycle, unreacted nickel alkoxide compound gas, reducing gas, and by-produced gas are exhausted from the deposition reaction chamber in the same way as the above-described exhaustion step, and then the next cycle is conducted.

In the formation of a nickel thin film by the ALD process, energy, such as plasma, light, and voltage, may be applied. The time when such energy is applied is not particularly limited; this time may be during the introduction of the nickel alkoxide compound gas in the raw material introduction step, at the time of heating in the precursor thin film formation step or the nickel thin film formation step, during the exhaustion of the system in the exhaustion step, or during the introduction of reducing gas in the nickel thin film formation step, and it also may be between the steps described above.

Moreover, the production of a thin film using the raw material for thin film formation of the present invention may include an annealing treatment conducted under an inert atmosphere, an oxidative atmosphere or a reducing atmosphere in order to attain better electrical properties after the deposition of a thin film. When step coverage is required, a reflow step may be provided. The temperature in this case is 250 to 1000° C., and preferably 300 to 500° C.

The thin film produced using the raw material for thin film formation of the present invention can be fabricated as a desired type of thin film, such as metal, oxide ceramics, nitride ceramics, and glass, by appropriately choosing precursor of other component, the reactive gas, and production conditions. Examples of the composition of the thin film to be produced include metallic nickel, nickel-based oxides, nickel-based nitrides, and nickel-based alloys such as Ni—Ti, Ni—Cr, Ni—V, Ni—Cu, Ni—Cr—Si, Ni—Cr—Al, Ni—W, AuGeNi, and $NiP_2$. The examples of the applications of these films include an electrode film, a barrier film, a resistance film, a magnetic film, a barrier metallic film for liquid crystals, a member for thin film solar cells, a member for semiconductor apparatuses, a nanostructure, a hydrogen storage material, a micro-electromechanical actuator.

EXAMPLES

The present invention is described in more detail below with reference to Examples. However, the present invention is not limited by the following Examples.

Example 1

Production of Compound No. 1

Under an argon gas atmosphere, a reaction flask was charged with 12.77 g of hexaamminenickel(II) chloride and 40.37 g of dehydrated toluene and was stirred at room temperature. A solution prepared by dissolving 15.17 g of sodium 1-(N,N-dimethylamino)-2-butoxide in 68.70 g of dehydrated toluene was added thereto slowly at room temperature. Subsequently, after refluxing for about 8 hours, filtration was conducted. Toluene was removed from the resulting filtrate, affording a solid residue. The solid residue was sublimed at 120° C. under a reduced pressure of 150 Pa, affording a green solid. The purification resulted in 60% recovery. The resulting green solid had a melting point of 84° C. and its elemental analysis and $^1$H-NMR analysis confirmed it to be the target compound, Compound No. 1. The results of these analyses are shown below. The result of TG-DTA is also presented below.

(Analytical Data)
(1) Elemental analysis (metal analysis: ICP-AES, chlorine analysis: TOX)
Nickel: 17.1% by mass (theoretical value: 20.2%), Na: less than 1 ppm, Cl: less than 1 ppm
C: 45.2% by mass, H: 9.1% by mass, N: 9.0% by mass (theoretical value: C: 49.5%, H: 9.7%, N: 9.6%)
(2) $^1$H-NMR (solvent: deuterated benzene) (chemical shift:multiplicity:the number of H)
(0.99:t:3) (1.28:m:2) (1.42:m:1) (2.0:m:4) (2.53:d:3) (3.32:m:1)
(3) TG-DTA (Ar 100 ml/min, temperature rising rate 10° C./min, the amount of sample: 9.172 mg)
50% mass loss temperature: 183° C.

Example 2

Production of Compound No. 3

Under an argon gas atmosphere, a reaction flask was charged with 12.54 g of hexaamminenickel(II) chloride and 36.27 g of dehydrated toluene and was stirred at room temperature. A solution prepared by dissolving 18.06 g of sodium 1-(N,N-dimethylamino)-2-hexoxide in 52.46 g of dehydrated toluene was added thereto slowly at room temperature. Subsequently, after refluxing for about 8 hours, filtration was conducted. Toluene was removed from the resulting filtrate, affording a solid residue. The solid residue was sublimed at 140° C. under a reduced pressure of 150 Pa, affording a green solid. The purification resulted in 68% recovery. The resulting green solid had a melting point of 96° C. and its elemental analysis and $^1$H-NMR analysis confirmed it to be the target compound, Compound No. 3. The results of these analyses are shown below. The result of TG-DTA is also presented below.

(Analytical Data)
(1) Elemental analysis (metal analysis: ICP-AES, chlorine analysis: TOX)
Nickel: 15.5% by mass (theoretical value: 16.9%), Na: less than 1 ppm, Cl: less than 1 ppm
C: 50.2% by mass, H: 9.9% by mass, N: 9.5% by mass (theoretical value: C: 55.4%, H: 10.5%, N: 8.1%)
(2) $^1$H-NMR (solvent: deuterated benzene) (chemical shift:multiplicity:the number of H)
(0.95:t:3) (1.39:m:6) (1.55:m:3) (1.99:m:1) (2.24:m:4) (2.54:d:3) (3.40:m:1)
(3) TG-DTA (Ar 100 ml/min, temperature rising rate 10° C./min, the amount of sample: 9.439 mg)
50% mass loss temperature: 223° C.

Example 3

Production of Compound No. 4

Under an argon gas atmosphere, a reaction flask was charged with 125.13 g of hexaamminenickel(II) chloride and 638 g of dehydrated toluene and was stirred at room temperature. A solution prepared by dissolving 165.30 g of sodium 1-(N,N-ethylmethylamino)-2-butoxide in 241.5 g of dehydrated toluene was added thereto slowly at room temperature. Subsequently, after refluxing for about 8 hours, filtration was conducted. Toluene was removed from the resulting filtrate, affording a liquid residue. The liquid residue was distilled under reduced pressure, and a fraction of 100 Pa at a tower top temperature of 105 to 106° C. was taken to afford a deep green liquid. The purification resulted in 80% recovery. Elemental analysis and $^1$H-NMR analysis confirmed that the resulting deep green liquid was the target compound, Compound No. 4. The results of these analyses are shown below. The result of TG-DTA is also presented below.

(Analytical Data)

(1) Elemental analysis (metal analysis: ICP-AES, chlorine analysis: TOX)

C: 46.5% by mass, H: 9.6% by mass, N: 8.5% by mass (theoretical value: C: 52.7%, H: 10.1%, N: 8.8%)

Ni: 17.8% by mass (theoretical value: 18.4%)

(2) $^1$H-NMR (solvent: deuterated benzene) (chemical shift:multiplicity:the number of H)

The NMR chart obtained is shown in FIG. 1.

(3) TG-DTA (Ar 100 ml/min, temperature rising rate 10° C./min, the amount of sample: 10.796 mg)

50% mass loss temperature: 195° C.

Example 4

Production of Compound No. 7

Under an argon gas atmosphere, a reaction flask was charged with 12.55 g of hexaamminenickel(II) chloride and 42.64 g of dehydrated toluene and was stirred at room temperature. A solution prepared by dissolving 18.06 g of sodium 1-(N,N-diethylamino)-2-butoxide in 61.2 g of dehydrated toluene was added thereto slowly at room temperature. Subsequently, after refluxing for about 8 hours, filtration was conducted. Toluene was removed from the resulting filtrate, affording a liquid residue. The liquid residue was distilled under reduced pressure, and a fraction of 120 Pa at a tower top temperature of 102 to 103° C. was taken to afford a deep green liquid. The purification resulted in 66% recovery. Elemental analysis and $^1$H-NMR analysis confirmed that the resulting deep green liquid was the target compound, Compound No. 7. The results of these analyses are shown below. The result of TG-DTA is also presented below.

(Analytical Data)

(1) Elemental analysis (metal analysis: ICP-AES, chlorine analysis: TOX)

C: 45.5% by mass, H: 9.1% by mass, N: 6.5% by mass (theoretical value: C: 55.4%, H: 10.5%, N: 8.1%)

Ni: 16.4% by mass (theoretical value: 16.9%)

(2) $^1$H-NMR (solvent: deuterated benzene) (chemical shift:multiplicity:the number of H)

Figure 2:
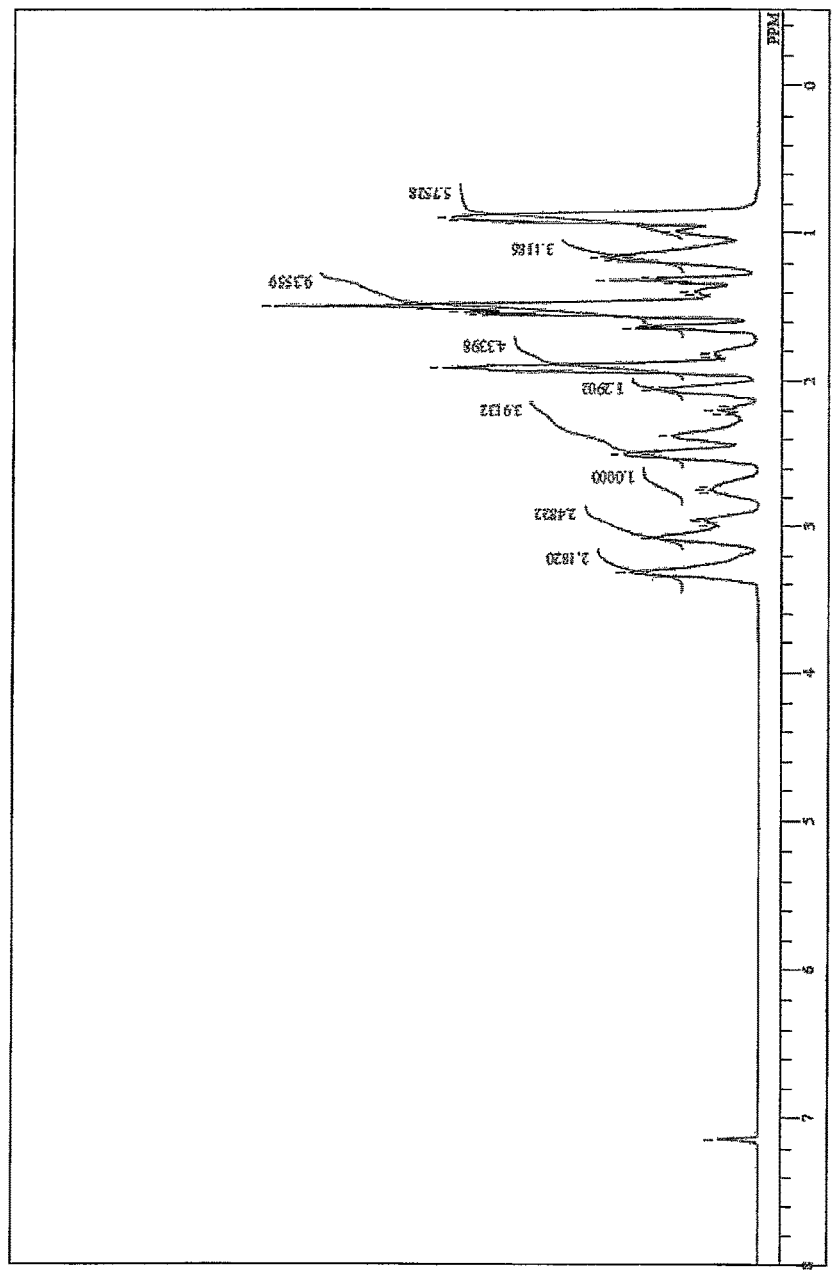
FIG. 2 is an NMR chart of the Compound No. 7 obtained in Example 4.

The NMR chart obtained is shown in FIG. 2.

(3) TG-DTA (Ar 100 ml/min, temperature rising rate 10° C./min, the amount of sample: 10.568 mg)

50% mass loss temperature: 206° C.

Evaluation of Physical Properties of Nickel Compound

For each of Compound Nos. 1 (Example 1), 3 (Example 2), 4 (Example 3), 7 (Example 4) obtained in the above-described Examples 1 to 4 and Comparative Compounds 1 (Comparative Example 1) and 2 (Comparative Example 2) provided below, the state of the compound at normal temperature and normal pressure was observed visually, a melting point was measured for solid compounds by using a micro melting point analyzer, and the boiling point of each compound was measured. Results are shown in Table 1.

Comparative Compound 1

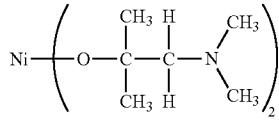

Comparative Compound 2

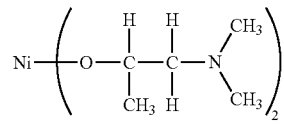

TABLE 1

| | Compound | State | Melting Point | Boiling Point |
|---|---|---|---|---|
| Example 1 | Compound No. 1 | Solid | 84° C. | 120° C./150 Pa |
| Example 2 | Compound No. 3 | Solid | 96° C. | 140° C./150 Pa |
| Example 3 | Compound No. 4 | Liquid | — | 105° C./100 Pa |
| Example 4 | Compound No. 7 | Liquid | — | 102° C./120 Pa |
| Comparative Example 1 | Comparative Compound 1 | Solid | 118~119° C. | 100° C./100 Pa[*1] |
| Comparative Example 2 | Comparative Compound 2 | Solid | 147° C. | 100° C./80 Pa[*1] |

[*1]An attempt of experiment failed to pass through a liquid state and resulted in sublimation.

Table 1 confirmed that Comparative Examples 1 and 2 are solids having melting points higher than 100° C., whereas Examples 1, 2, 3, and 4 are each a liquid or a low-melting compound that turns to a liquid on slight heating.

It was also confirmed that the solid compounds of Comparative Examples 1 and 2 are highly sublimable and, when they are used as a raw material for chemical vapor deposition, the raw material is difficult to be delivered and fed in a stable liquid state. When such a highly sublimable compound is used as the raw material, it is difficult, in the step of introducing the raw material to a substrate in a chemical vapor deposition process, to control the fed amount of the raw material to the substrate. Since the alkoxide compound of the present invention is a liquid at normal temperature or turns to a liquid on slight heating, the compound is advantageous in that it is possible to deliver and feed the raw material comprising the compound stably to the substrate and in that it is easy to control the fed amount in the step of introducing the raw material to a substrate in a chemical vapor deposition process.

It was confirmed from these that the alkoxide compound of the present invention is suitable as a raw material for thin film formation.

The invention claimed is:

1. A raw material for film formation comprising an alkoxide compound represented by one of the following compounds:

Compound No. 4

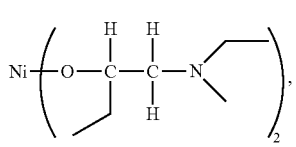

Compound No. 10

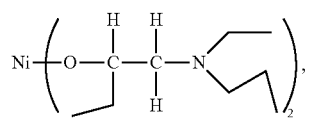

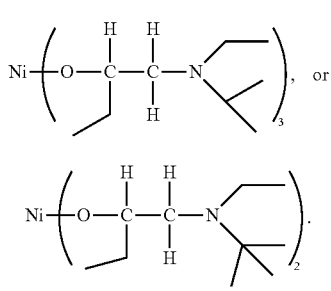

Compound No. 13, or

Compound No. 16

2. The raw material for thin film formation according to claim 1 to be used as a raw material for chemical vapor deposition.

3. The raw material for thin film formation according to claim 2, the raw material comprising a precursor comprising the alkoxide compound and optionally a precursor excluding the alkoxide compound, wherein the precursor excluding the alkoxide compound is in a proportion of from 0 to 10 mol per mol of the alkoxide compound, and the raw material is delivered and fed by a vapor delivery method or a liquid delivery method in thin film production.

4. The raw material for thin film formation according to claim 2, the raw material comprising an organic solvent and a precursor comprising the alkoxide compound and optionally a precursor excluding the alkoxide compound, wherein the content of the precursor comprising the alkoxide compound is 0.01 to 2.0 mol/liter, the precursor excluding the alkoxide compound is in a proportion of from 0 to 10 mol per mol of the alkoxide compound, and the raw material is delivered and fed by a liquid delivery method in thin film production.

5. The raw material for thin film formation according to claim 2, the raw material comprising a precursor comprising the alkoxide compound and a precursor excluding the alkoxide compound, wherein the precursor excluding the alkoxide compound is in a proportion of from 0 to 10 mol per mol of the alkoxide compound, and the raw material is delivered and fed by a vapor delivery method or a liquid delivery method in thin film production.

6. The raw material for thin film formation according to claim 2, the raw material comprising a precursor comprising the alkoxide compound, and the raw material is delivered and fed by a vapor delivery method or a liquid delivery method in thin film production.

7. The raw material for thin film formation according to claim 1, the raw material comprising an organic solvent and a precursor comprising the alkoxide compound and a precursor excluding the alkoxide compound, wherein the content of the precursor comprising the alkoxide compound is 0.01 to 2.0 mol/liter, the precursor excluding the alkoxide compound is in a proportion of from 0 to 10 mol per mol of the alkoxide compound, and the raw material is delivered and fed by a liquid delivery method in thin film production.

8. The raw material for film formation according to claim 1, wherein the alkoxide compound is in a liquid state under room temperature and room pressure.

9. The raw material for film formation according to claim 1, further comprising at least one solvent selected from the group consisting of ethyl acetate, butyl acetate, methoxyethyl acetate, ethylene glycol monomethyl ether, ethylene glycol monoethyl ether, ethylene glycol monobutyl ether, diethyleneglycol, tetrahydrofuran, tetrahydropyran, ethylene glycol dimethyl ether, diethylene glycol dimethyl ether, triethylene glycol dimethyl ether, dibutyl ether, dioxane, methyl butyl ketone, methyl isobutyl ketone, ethyl butyl ketone, dipropyl ketone, diisobutyl ketone, methyl amyl ketone, cyclohexanone, methylcyclohexanone, hexane, cyclohexane, methylcyclohexane, dimethylcyclohexane, ethylcyclohexane, heptane, octane, toluene, and xylene 1-cyanopropane, 1-cyanobutane, 1-cyanohexane, cyanocyclohexane, cycanobenzene, 1,3-dicyanopropane, 1,4-dicyanobutane, 1,6-dicyanohexane, 1,4-dicyanocyclohexane, 1,4-dicyanobenzene, pyridine and lutidine.

10. The raw material for film formation according to claim 9, wherein a total amount of the alkoxide compound and other precursor(s) in the organic solvent is 0.01 to 2.0 mol/liter.

11. The raw material for film formation according to claim 9, wherein a total amount of the alkoxide compound and other precursor(s) in the organic solvent is 0.05 to 1.0 mol/liter.

12. The raw material for film formation according to claim 1, wherein the alkoxide compound is the Compound No. 4 having a 50% mass loss temperature of 195° C. and a boiling point of 102° C. at 120 Pa:

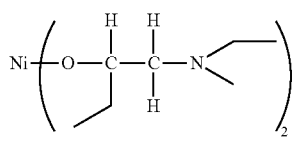

Compound No. 4

13. A raw material for film formation comprising an alkoxide compound represented by the following:

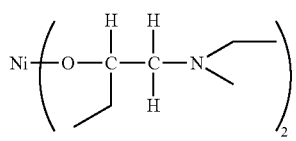

Compound No. 4 having a 50% mass loss temperature of 195° C. and a boiling point of 102° C. at 120 Pa.

* * * * *